(12) United States Patent
Rovnyi et al.

(10) Patent No.: US 10,470,441 B2
(45) Date of Patent: *Nov. 12, 2019

(54) ANIMAL MONITOR

(71) Applicant: GRAVITY LIMITED, Auckland (NZ)

(72) Inventors: Alexandre Nikolaevich Rovnyi, Cambridge (NZ); Berri Antonius Schroder, Auckland (NZ)

(73) Assignee: GRAVITY LIMITED, Auckland (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 16/059,042

(22) Filed: Aug. 9, 2018

(65) Prior Publication Data
US 2018/0359998 A1 Dec. 20, 2018

Related U.S. Application Data

(63) Continuation of application No. 15/024,196, filed as application No. PCT/NZ2014/000206 on Sep. 23, 2014, now Pat. No. 10,070,626.

(30) Foreign Application Priority Data

Sep. 23, 2013 (NZ) ........................ 615764

(51) Int. Cl.
*A61B 5/11* (2006.01)
*A01K 29/00* (2006.01)
(Continued)

(52) U.S. Cl.
CPC .......... *A01K 29/005* (2013.01); *A01K 11/004* (2013.01); *A61B 5/0022* (2013.01);
(Continued)

(58) Field of Classification Search
CPC .............. A01K 29/005; A01K 29/0283; A61B 2503/40; A61B 5/746; A61B 2562/0219;
(Continued)

(56) References Cited

U.S. PATENT DOCUMENTS

| 2003/0205208 A1* | 11/2003 | Bar-Shalom | ............ G06F 19/00 |
| | | | 119/859 |
| 2009/0182207 A1* | 7/2009 | Riskey | ................. A61B 5/0031 |
| | | | 600/302 |

(Continued)

FOREIGN PATENT DOCUMENTS

| EP | 2027770 A2 | 2/2009 |
| GB | 2437250 A | 10/2007 |

(Continued)

OTHER PUBLICATIONS

Foreign Communication from a Related Counterpart Application, International Search Report and Written Opinion dated Mar. 5, 2015, International Application No. PCT/NZ2014/000206 filed on Sep. 23, 2014.

(Continued)

*Primary Examiner* — Benyam Haile

(57) ABSTRACT

An animal monitor comprising a microcontroller; at least one three-axis accelerometer; an energy source; a charger; and a communications system, including a wireless transmitter and receiver.

28 Claims, 5 Drawing Sheets

(51) Int. Cl.
*A61B 5/00* (2006.01)
*G16H 40/67* (2018.01)
*A01K 11/00* (2006.01)
*G06F 19/00* (2018.01)
*G08B 21/18* (2006.01)
*G01G 9/00* (2006.01)
*G01G 7/02* (2006.01)
*A01K 5/02* (2006.01)
*G01G 7/00* (2006.01)
*G01G 7/04* (2006.01)
*G01G 17/08* (2006.01)

(52) U.S. Cl.
CPC ............... *A61B 5/11* (2013.01); *A61B 5/1118* (2013.01); *A61B 5/7278* (2013.01); *G06F 19/00* (2013.01); *G16H 40/67* (2018.01); *A01K 5/0283* (2013.01); *A61B 5/1112* (2013.01); *A61B 5/6802* (2013.01); *A61B 5/6822* (2013.01); *A61B 5/6823* (2013.01); *A61B 5/6831* (2013.01); *A61B 5/746* (2013.01); *A61B 2503/40* (2013.01); *A61B 2562/0219* (2013.01); *A61B 2562/08* (2013.01); *G01G 7/00* (2013.01); *G01G 7/02* (2013.01); *G01G 7/04* (2013.01); *G01G 9/00* (2013.01); *G01G 17/08* (2013.01); *G08B 21/182* (2013.01)

(58) Field of Classification Search
CPC ....... A61B 5/6822; A61B 5/11; A61B 5/6831; A61B 5/1118; A61B 5/6802; A61B 5/6823; G01G 7/00; G01G 7/02; G01G 7/04; G01G 9/00; G01G 17/08; G08B 21/182
See application file for complete search history.

(56) References Cited

U.S. PATENT DOCUMENTS

| | | | | |
|---|---|---|---|---|
| 2011/0311109 | A1* | 12/2011 | Demarais | G06T 7/0012 382/110 |
| 2012/0089340 | A1* | 4/2012 | Huisma | A01K 5/02 702/19 |
| 2014/0195023 | A1* | 7/2014 | Statham | A61B 5/1038 700/91 |
| 2014/0333439 | A1* | 11/2014 | Downing | A01K 29/005 340/573.3 |
| 2015/0034396 | A1 | 2/2015 | Tchertkov et al. | |

FOREIGN PATENT DOCUMENTS

| | | |
|---|---|---|
| WO | WO2001067853 | 9/2001 |
| WO | WO2011120529 A1 | 10/2011 |
| WO | WO2015041548 A1 | 3/2015 |

OTHER PUBLICATIONS

Foreign Communication from a Related Counterpart Application, International Preliminary Report on Patentability dated Apr. 7, 2016, International Application No. PCT/NZ2014/000206 filed on Sep. 23, 2014.

Office Action dated Jul. 21, 2017, U.S. Appl. No. 15/024,196, filed Mar. 23, 2016.

Final Office Action dated Nov. 3, 2017, U.S. Appl. No. 15/024,196, filed Mar. 23, 2016.

Notice of Allowance dated May 7, 2018, U.S. Appl. No. 15/024,196, filed Mar. 23, 2016.

* cited by examiner

Erich Reichel, Bundesgynasium und Bundesrealgymnasium Graz, Austria

Relative stiffness $k_{rel}$, changed less than half a decade over a mass range of four to five fold

ANIMAL MONITOR

CROSS-REFERENCE TO RELATED APPLICATIONS

The present application is a continuation of and claims priority to U.S. application Ser. No. 15/024,196, filed on Mar. 23, 2016 and entitled, "ANIMAL MONITOR" which is a National Stage Filing under 35 U.S.C. 371 of International Application No. PCT/NZ2014/000206, filed Sep. 23, 2014, entitled "ANIMAL MONITOR," which claims priority to New Zealand Application No. NZ 615764 filed on Sep. 23, 2013 with the Intellectual Property Office of New Zealand, each of which are incorporated herein by reference in their entirety for all purposes.

FIELD OF THE INVENTION

The present invention relates generally animal monitoring and in particular to a device, system and method for monitoring the wellbeing on animals.

BACKGROUND

Having real time information is important in any industry. Real time monitoring of farm animals can help improve productivity and profitability. At present animals may be monitored for condition and weight gain periodically such as when they are yarded. It would be desirable to be able to monitor animal health, wellness and weight gain without the need to yard the animals.

Thus there is a need for an animal monitor that improves that ability to monitor an animal's wellbeing or at least provides the public or industry with a useful choice.

SUMMARY OF THE INVENTION

In one embodiment the present invention consists in an animal monitor comprising: a microcontroller; at least one three-axis accelerometer; an energy source; a charger; and a communications system, including a wireless transmitter and receiver.

Preferably the animal monitor additionally includes at least one sound sensor.

Alternatively the animal monitor additionally includes at least two sound sensors.

Preferably the at least one three-axis accelerometer is at least two three-axis accelerometers.

Preferably the communications system includes a Wi-Fi transmitter and receiver.

Preferably the communications system includes a cellular transmitter and receiver.

Preferably the charger is a solar charger.

Preferably the animal monitor additionally includes a solar panel.

Preferably the animal monitor additionally includes an array of solar cells.

Preferably the charger obtains energy from the movement of the animal.

Preferably the charger obtains energy from radio waves.

Preferably the form of the animal monitor is an ear tag.

Alternatively the form of the animal monitor is a collar.

Alternatively the form of the animal monitor is a necklace.

Alternatively the form of the animal monitor is an implant.

Preferably the microcontroller is programmed to monitor characteristics of an animal.

Preferably microcontroller is programmed to record data.

Preferably the recorded data includes the frequency of acceleration during movement.

Preferably the recorded data includes distance traveled.

In a further embodiment the present invention is a method of monitoring at least one animal using a processor, the method comprising the steps of: receiving data from at least one animal monitor attached to an animal; storing the data in association with an identifier of the animal that the animal monitor is attached to; and analysing the data to calculate information on the animal with the animal monitor attached, wherein the information includes at least the weight of the animal.

Preferably the weight m of an animal is calculated using the formula $$m = \frac{K}{(2 \cdot \pi \cdot f)^2}$$

where K is the matrices of stiffness for the three degree of freedom (3DoF), and f is the frequency of the acceleration of the body during locomotion.

Preferably the method including the step of analysing the data to calculate information on the animal with the animal monitor attached including monitoring the cud chewing frequency of the animal.

Preferably the method including the step of raising an alarm if the cud chewing frequency of the animal drops below a desired level.

Preferably the method including the step of monitoring the wellbeing of the animal the animal monitor is attached to.

Preferably the wellbeing of an animal is calculated using a spectral centroid calculated as the weighted mean of the frequencies present in the signal of acceleration using a Fourier transform, with the magnitudes as the weights:

$$\text{Wellbeing Rank} = \frac{\sum_{n=0}^{N-1} f(n)x(n)}{\sum_{n=0}^{N-1} x(n)}$$

where x(n) represents the weighted frequency value, or magnitude, of bin number n, and f(n) represents the centre frequency of that bin.

Preferably the method including the step of raising an alarm if the wellbeing rank of the animal drops below a desired level.

Preferably the method including the step of receiving data on the growth of the animal antlers; and calculating information on the growth of the antlers based on the received data.

Preferably the method including the step of receiving and storing data on the animal from other data sources.

Preferably the other data sources includes a scale for measuring weight.

In a further embodiment the present invention includes an animal monitoring system comprising: a processor; memory; storage; and a communication device, the processor programmed to: receiving data from at least one animal monitor attached to an animal; storing the data in association with an identifier of the animal that the animal monitor is attached to; and analysing the data to calculate information on the animal with the animal monitor attached, wherein the information calculated includes at least the weight of the animal.

Preferably the weight m of an animal is calculated using the formula $$m = \frac{K}{(2 \cdot \pi \cdot f)^2}$$

where K is the matrices of stiffness for the three degree of freedom (3DoF), and f is the frequency of the acceleration of the body during locomotion.

Preferably the processor is programmed to calculate information on the animal with the animal monitor attached including monitoring the cud chewing frequency of the animal.

Preferably the processor is programmed to raise an alarm if the cud chewing frequency of the animal drops below a desired level.

Preferably the processor is programmed to monitor the wellbeing of the animal the animal monitor is attached to.

Preferably the wellbeing of an animal is calculated using a spectral centroid calculated as the weighted mean of the frequencies present in the signal of acceleration using a Fourier transform, with the magnitudes as the weights:

$$\text{Wellbeing Rank} = \frac{\sum_{n=0}^{N-1} f(n)x(n)}{\sum_{n=0}^{N-1} x(n)}$$

where x(n) represents the weighted frequency value, or magnitude, of bin number n, and f(n) represents the centre frequency of that bin.

Preferably the processor is programmed to raise an alarm if the wellbeing rank of the animal drops below a desired level.

Preferably the processor is programmed to: receive data on the growth of the animal antlers; and calculate information on the growth of the antlers based on the received data.

Preferably the processor is programmed to receiving and storing data on the animal from other data sources.

Preferably the other data sources includes a scale for measuring weight.

It is acknowledged that the terms "comprise", "comprises" and "comprising" may, under varying jurisdictions, be attributed with either an exclusive or an inclusive meaning. For the purpose of this specification, and unless otherwise noted, these terms are intended to have an inclusive meaning—i.e. they will be taken to mean an inclusion of the listed components that the use directly references, but optionally also the inclusion of other non-specified components or elements.

BRIEF DESCRIPTION OF THE DRAWINGS

Embodiments of the present invention will now be described, by way of example only, with reference to the accompanying drawings, in which.

DETAILED DESCRIPTION OF THE INVENTION

Figure 4:
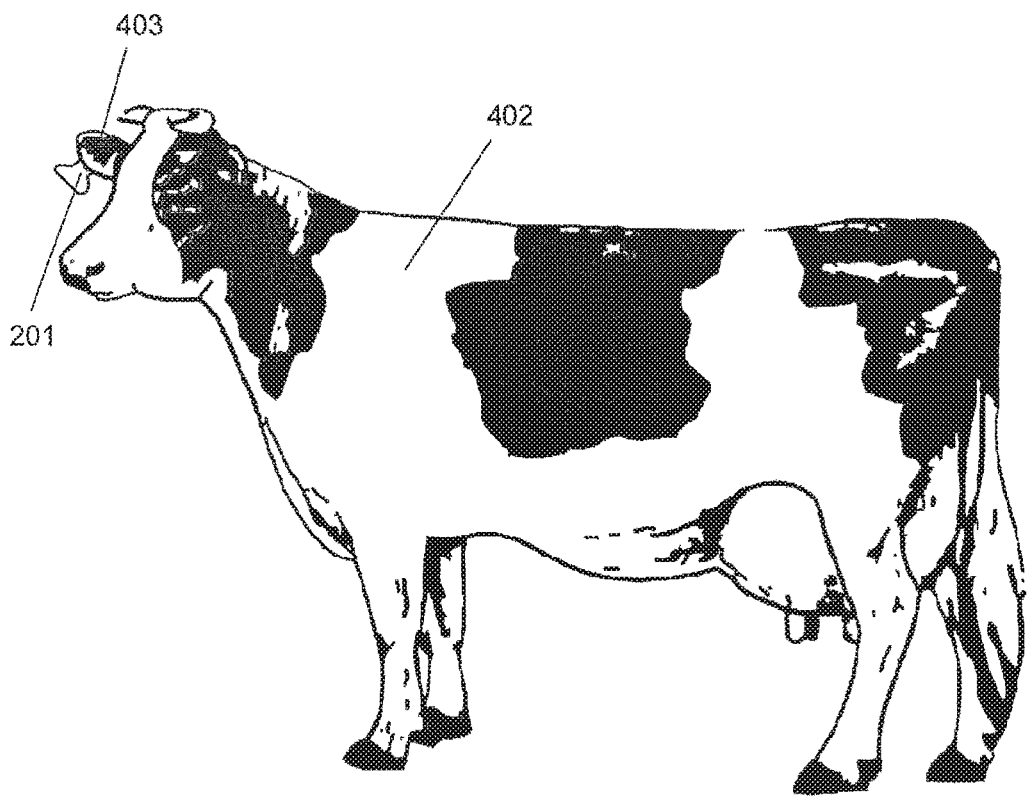
FIG. 4 is an illustration of a cow with the animal monitor of the present invention.
Figure 5:
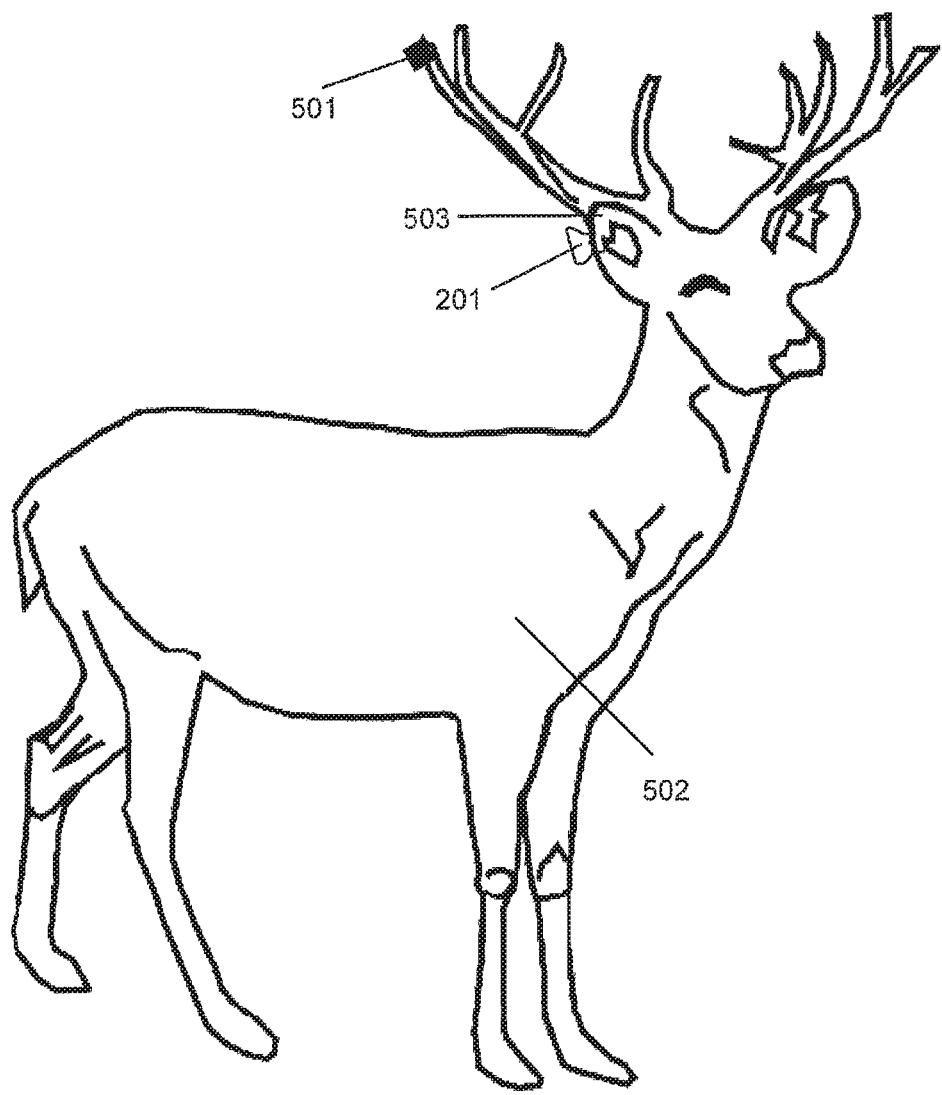
FIG. 5 is an illustration of a deer with the animal monitor and velvet monitor of the present invention.

Embodiments of the present invention are described herein with reference to an animal monitoring device such as an electronic ear tag, animal information processing system and a method for obtaining and processing information on an animal. The animals that may be monitored with the present invention include but are not limited to cattle, dairy cows, sheep, goats, pigs, horse, essentially any domesticated animal and wild animals. Referring to FIG. 4 a cow 402 with the animal monitor 201 attached to an ear 403 is illustrated. Referring to FIG. 5 a deer 502 with the animal monitor 201 attached to the ear 503 is shown.

In summary, the animal information processing system includes at least a processor, one or more memory devices or an interface for connection to one or more memory devices, input and output interfaces for connection to external devices in order to enable the system to receive and operate upon instructions from one or more users or external systems, a data bus for internal and external communications between the various components, and a suitable power supply. Further, the system may include one or more communication devices (wired or wireless) for communicating with external and internal devices, and one or more input/output devices, such as a display, pointing device, keyboard, operating buttons or printing device.

The processor is arranged to perform the steps of a program stored as program instructions within the memory device. The program instructions enable the various methods of performing the invention as described herein to be performed. The program instructions may be developed or implemented using any suitable software programming language and toolkit, such as, for example, a C-based language. Further, the program instructions may be stored in any suitable manner such that they can be transferred to the memory device or read by the processor, such as, for example, being stored on a computer readable medium. The computer readable medium may be any suitable medium, such as, for example, solid state memory, magnetic tape, a compact disc (CD-ROM or CD-R/W), memory card, flash memory, optical disc, magnetic disc or any other suitable computer readable medium including organic based systems, for example DNA memory chip.

It will be understood that the system herein described includes one or more elements that are arranged to perform the various functions and methods. The following portion of the description is aimed at providing the reader with an example of a conceptual view of how various modules and/or engines that make up the elements of the system may be interconnected to enable the functions to be implemented. Further, the following portion of the description explains in system related detail how the steps of the herein described method may be performed.

It will be understood that the arrangement and construction of the modules, systems, devices or engines may be adapted accordingly depending on system and user requirements so that various functions may be performed by different modules, systems, devices or engines to those described herein, and that certain modules, systems, devices or engines may be combined into single modules, systems, devices or engines.

It will be understood that the modules, systems, devices or engines described may be implemented and provided with instructions using any suitable form of technology. For example, the modules, systems, devices or engines may be implemented or created using any suitable software code written in any suitable language, where the code is then compiled to produce an executable program that may be run on any suitable computing system. Alternatively, or in conjunction with the executable program, the modules, systems, devices or engines may be implemented using any suitable mixture of hardware, firmware and software. For example, portions of the modules may be implemented using an application specific integrated circuit (ASIC), a system-on-a-chip (SoC), field programmable gate arrays (FPGA) or any other suitable adaptable or programmable processing device.

The methods described herein may be implemented using a general purpose computing system specifically programmed to perform the described steps. Alternatively, the methods described herein may be implemented using a specific device or appliance.

In order to monitor and assess various characteristics of an animal the animal will be fitted with a monitor (the animal monitor). The animal monitor may take various physical forms, without limiting the form of the animal monitor it may take the form of an ear tag, a collar, a necklace or an implant.

In one form the animal monitor is an ear tag, similar to those used for animal identification in particular the tags used for cattle, deer, sheep, goats and pigs.

Figure 2:
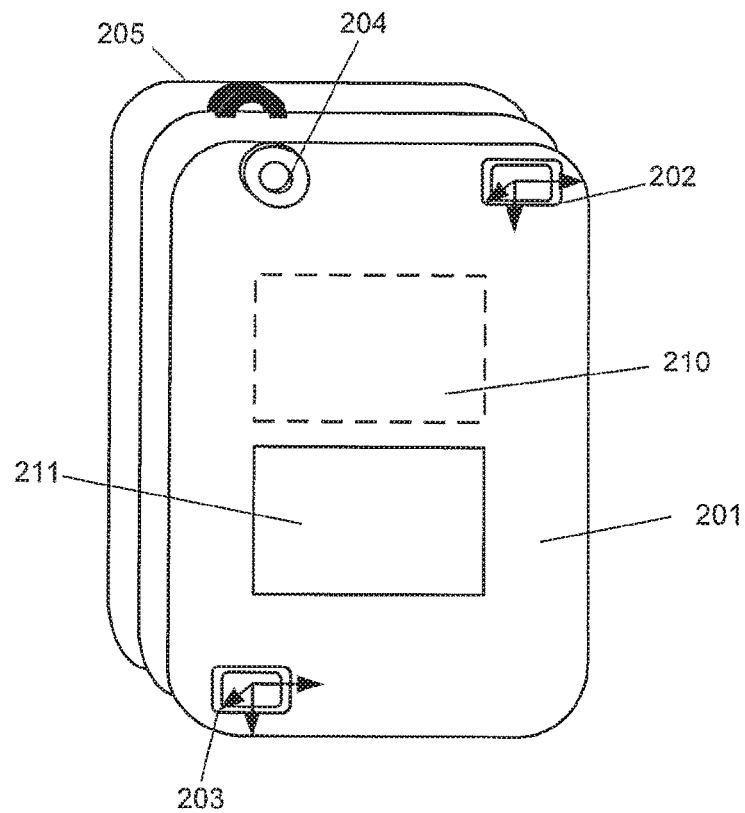
FIG. 2 is an exemplary embodiment of the animal monitoring device of the present invention.

Referring to FIG. 2 the monitor 201 would include a microcontroller ("MCU") 210. The microcontroller 210 is essentially a small computer on a single integrated circuit containing a processor core, memory, and programmable input/output peripherals. Program memory in the form of NOR flash or OTP may be included on chip, as well as a typically small amount of RAM. The microcontroller will be programmed with a firmware to allow the microcontroller 210 to operate in accordance with the present invention.

The animal monitor 201 will included at least one, three-axis accelerometer 202 and may include an additional three-axis accelerometer 203. The 201 monitor 210 would also include an energy source 211 such as an EnerChip smart solid state batteries. The energy source 211 would include an energy management controller with additional energy management optionally being programmed into the microcontroller 210.

The monitor 201 would also include a charger for the energy source 211, optionally the charger could be built into the energy source 211. In one embodiment a solar panel or an array of solar cells would be used, but a charger that uses the energy from animal movement, from radio waves or any other suitable charging method or a combination of charging methods could also be used.

Figure 1:
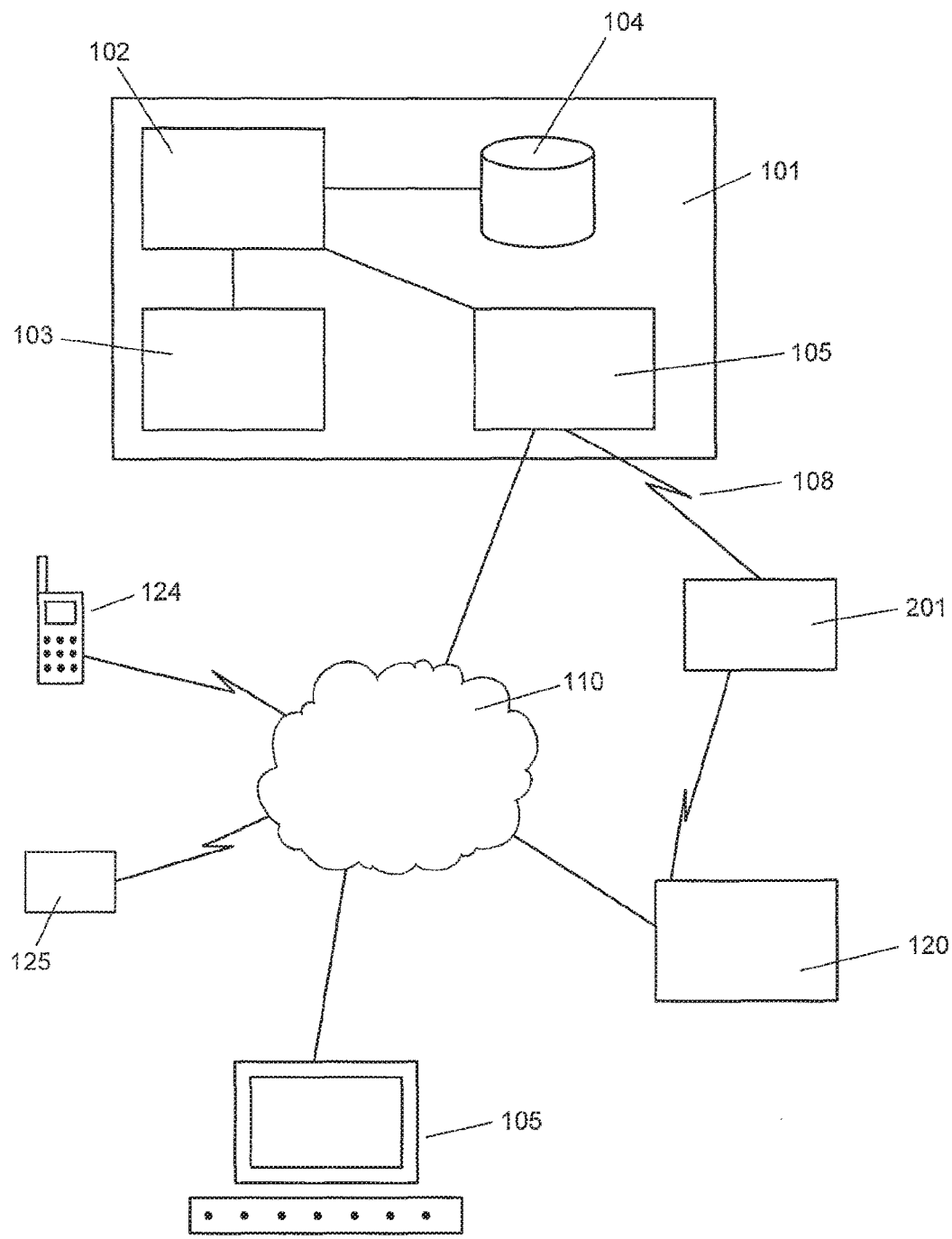
FIG. 1 is an exemplary embodiment of the animal monitoring system of the present invention.

The animal monitor 201 further includes a communication system. The communication system is not limited as to form as long as it allows the animal monitor 201 to communicate with external devices. Examples of the communication system include a communication system that can communicate using hard wire (such as a farm fence wire), drones, amplification by water, aerial transmission, Wi-Fi, any other license-free frequencies, commercial telephone transmission services and frequencies including cellular, Bluetooth, satellite link transmissions, and free in space optical communications. The communication system would be used to allow the animal monitor 201 to communicate with an animal monitoring server 101 as seen in FIG. 1. The animal monitoring server 101 stores and processes the data received from the animal monitor 201 which is located on the animal.

Optionally the animal monitor 201 would include sound sensors with rear and front sound ports 204, 205 or a plurality of sound sensors.

Data from a plurality of animal monitors 201 would be sent by the animal monitors 201 to an animal monitoring server 101 described below. Whenever data is sent the data will include an identifier of the animal monitor 201 so that the data may be related to an individual animal when multiple animal monitors 201 are used in a system.

Referring to FIG. 1 the animal monitoring server 101 would include a CPU 102, memory 103, storage such as a hard drive 104 and a communication device 105 such as an Ethernet controller. The animal monitoring server 101 is preferably connected to a communications network 110 to allow the animal monitoring server 101 to send and receive information from a plurality of animal monitors 201. Further the animal monitoring server 101 is preferably connected to the internet and may be accessed remotely by a user computer or appliance 105 seeking information via a web browser or other computer application.

In one embodiment the animal monitoring server 101 would be able to update the firmware and application software on the animal monitors 201 as improvements are made.

The animal monitoring server 101 would also be able to receive data on the monitored animals from other sources. Non-limiting examples include the weight of an animal as it is weighed on traditional electronic scales, information on the actual milk production, wool production and/or velvet production of the animal.

The animal monitoring server 101 may receive information from the plurality of animal monitors 201 and the other information sources via an intermediary device 120 or an application that can run on a computer at a farm. The intermediary device may be a dedicated communications appliance.

The animal monitoring server 101 will also have an interface, in one embodiment a web interface that a user can enter data on an animal.

In an alternative embodiment an application for a user input device such as a computer, laptop, netbook or a mobile communications device may be provided. Such data will include but is not limited to the animal type, animal breed, date of birth or age, sex, and the National Animal Identification and Tracing (NAIT) number of the animal. Additionally the animal monitoring server 101 would have information including an identifier of the animal monitors 201 (one or more) that are attached to each animal.

Whenever the animal monitoring server 101 calculates information on an animal based on information received from the animal monitor 201 or receives information on an animal from another source for example the weight of the animal the animal monitoring server 101 stores the information and the date the information was received or calculated associated with an identifier of the animal monitor 101.

The animal monitoring server or appliance 101 may additionally be connected to the animal monitors 201 via a communications network 108, as above the type and choice of such network is not limited.

Further it is envisaged that the animal monitoring server 101 would be able to provide alerts to a user via a cellular message to a cellular telephone 124 or via other messaging device 125. The alert may also be generated in another form such as an email or a light (red or otherwise) flashing.

The animal monitors 201 provide data that the animal monitoring server 101 uses to calculate/generate information on the animal that the animal monitor 201 is attached to. Non-limiting examples of the information that could be provided and used are described below. Whether or not the examples below would be used in monitoring a particular animal would depend on the animal type, but the type of monitoring may also depend on the individual animal.

While the information below is described as calculated by the animal monitoring server 101, some or all of the information could be calculated by the animal monitor 201.

In a further embodiment a multi-access gyro when used with a multi-axis accelerometer and magnetometer can be used to form a combined inertial measurement unit to give a total movement monitoring solution. The information from the monitors can be processed in a number of ways to indicate speed, direction and derived position from a reference point. These monitors may be combined with GPS when available. This group of sensors provides for position and overall motion indication.

Weight or Weight Gain

The animal monitoring server 101 can estimate the weight of the animal. Weight estimation is based on the fact that the value of an object's mass is a unique property, independent of the measurement method, (ie gravitational methods used in conventional scales). Inertial mass is measured with the use of an inertial balance, or spring loaded pan. A spring loaded pan method is a dynamic measurement and this method is utilized in the animal monitor 201.

To estimate the weight of an animal the animal monitor 201, monitors the movement of the animal using at least one accelerometer until it detects a pattern of free walking or running. Then the monitor 201 assesses the suitability of the sample of free walking or running for estimating weight. The suitability is accessed based on minimum of the variations of the stride duration or speed variations or variation of acceleration data. The suitability of a data sample also depends on the desired accuracy of weight gain/loss measurement. As described below the weight/weight gain is determined by measured frequency and the accuracy of the measure frequency is proportional to 1/T where the T is the duration of the data sample. A short data sample/record gives low accuracy of measurement of weight;

If the sample is suitable for estimating weight the monitor 201 stores the sample for forwarding to the animal monitoring server 101. In some circumstances the sample will be forwarded immediately in other circumstances it will be stored until a suitable communication means is available, such as when a drone flies over, if the animal being monitored is in a remote location. The information stored by the animal monitor 201 includes the speed of the animal and the frequency of oscillations during locomotion. The animal monitoring server 101 then estimates the weight of the animal based on Hook's Law.

It is known that conversion of potential energy to kinetic during the movement of the animal is governed by the principal of a spring loaded mass. The spring stiffness is represented as muscular skeletal attributes of the animal for example tendons and joints. Based on this an assessment of the weight is made based on Hook's Law and harmonic oscillator principle, where the oscillation frequency of the mass attached to a spring is inversely proportional to the mass.

In the preferred embodiment weight data is stored by the animal monitoring server 101 from a number of animals with known weights. Using the speed of the animal and the frequency of oscillations during locomotion as keys the animal monitoring server 101 can look up a table which consists of the whole body stiffness coefficients matrices and the relevant Froude numbers for the specific speeds and types of a gait.

Figure 6:
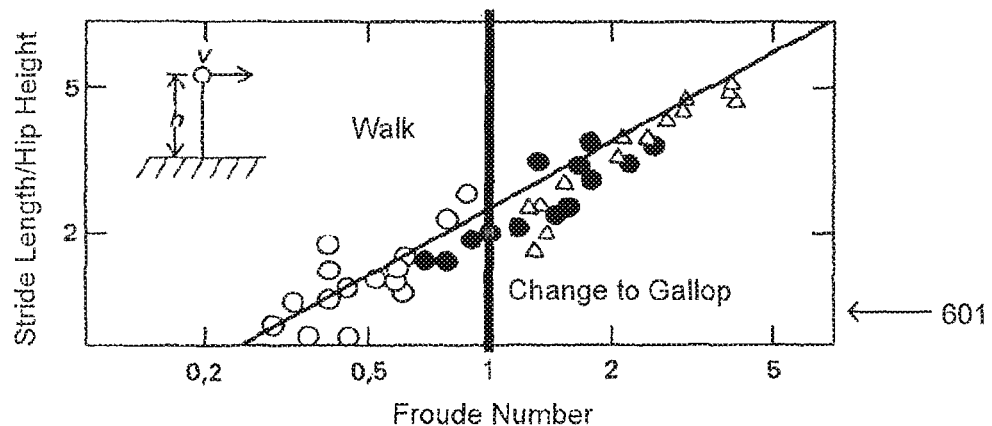
FIG. 6 is a graph showing the relationship between the Froude number and stride/hip height.
Figure 7:
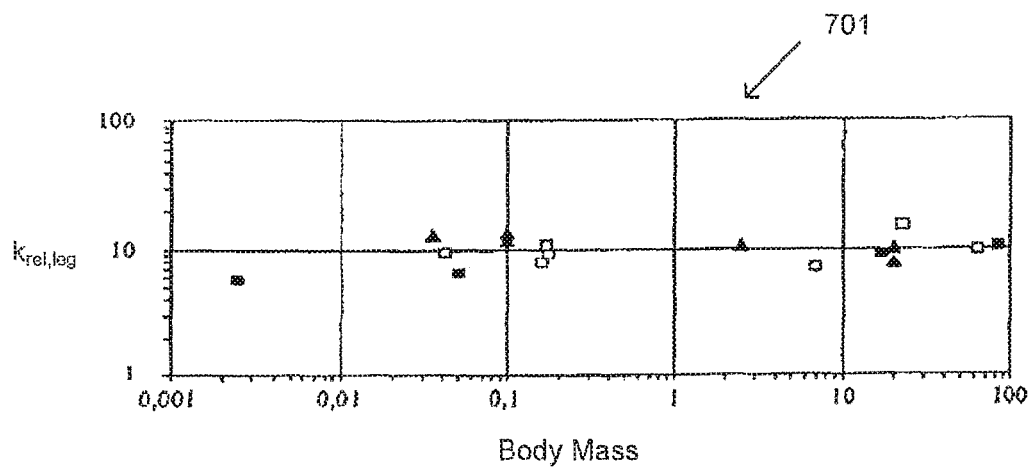
FIG. 7 is a graph showing the relationship between body mass and relative stiffness.

As seen in FIG. 6 the Froude number has a direct relationship 601 to the stride and hip height when compared to speed. Further as seen in FIG. 7 research has shown that relative whole body stiffness 701 is related to body mass.

Thus the body mass changes estimation can be established, as:

$$\Delta m = \frac{Fn}{(2 \cdot \pi \cdot \Delta f)^2}$$

where $\Delta m$—mass changes, $Fn$—Froude number, $\Delta f$—changes in frequency of the acceleration of the body during locomotion Further the body mass can be established, as:

$$m = \frac{K}{(2 \cdot \pi \cdot f)^2}$$

where K is the matrices of stiffness for the three degree of freedom (3DoF), and f is the frequency of the acceleration of the body during locomotion.

Accordingly based on this method the animal monitoring server 101 can calculate and store both the change in weight and the actual estimated weight of an animal. While this has been described as being calculated using the animal monitoring server 101, in an alternative embodiment the animal monitor 201 may store the tables in firmware and perform the weight calculation.

Alternatively weight may be measured using a measurement system based on the model of the tag movement governed (described) by $$F = E \cdot S, \text{ where}$$

F termed as stress tensor;
S termed as strain tensor;
E elasticity tensor

Based on tensor resolved solutions the weight measurement W could be evaluated, for example, as outputs of the model of the spring loaded pan or Hook's Law:

$$W = k/(2 \cdot \pi \cdot f)^2, \text{ where}$$

k stiffness coefficient;
f frequency
or as solutions of impulse of the forces acting upon the tag:

$$W = \frac{P \cdot \Delta t}{\Delta V},$$

where
P termed as acting force;
ΔV changes of a velocity;
Δt time duration of the velocity change.

Cud Chewing

The animal monitor 201 of the present invention would for this use have at least two three-axis accelerometers 202, 203 fitted at a known distance and at least two sound sensors 204, 205 with ports on opposite sides of animal monitor 201. This allows the sound sensors to operate independently.

One of the sound sensors would be directed to the ear side of the monitored animal and process sound transduced via bone conduction. The other sound sensor would processing ambient sound and could in one embodiment be used to detect rustlers.

Animal body locomotion in general is a status of a three degrees of freedom system without pitch, yew and roll, and can be determined by one 3-axis accelerometer. An animal monitor 201 implemented as an ear tag has six degrees of freedom and the tags rotational, centrifugal and gravitation accelerations are mixed, and cannot be resolved with only one 3-axis accelerometer output. In order to obtain six degrees of freedom acceleration data with regarding to translational and rotational motion we need to resolve multiple acceleration signals and a minimum of two 3-axis accelerometers to distinguish ear tag attitudes from body movements are needed.

The animal monitor 201 would use the received information from the sensors including the sound sensors 204, 205 and a lookup table consisting of a list of conceivable patterns of the incoming information to identify the activity that corresponds to the patterns. The activities are activities in the animal's daily routine for example: walking, lying and resting, or specific to the breed cud chewing.

Information on the speed of the animal and the distance the animal has traveled are also able to be stored by the animal monitor 201 to be later sent the animal monitoring server 101.

Information on the activities of the animal are then sent to the animal monitoring server 101.

Cud chewing is important, all animals have to eat. If an animal is unwell as a result of ill health or trauma, generally speaking the first thing that happens is that the animal's eating patterns change. The frequency of chewing, and therefore food intake, decreases. With a cow it is more noticeable as the cow is a ruminant. This means that it bites off the grass, swallows it, which then is stored in the first stomach. It then regurgitates the grass from its first stomach by belching, masticates it again and swallows it once again. This goes into the second stomach. This is repeated once again before the grass goes into the large intestine. Most cows need to cud chew 60-80 times a minute. So if they are unwell they don't chew. The cud chewing data identified by the animal monitor 201 would be sent on a regular basis to the animal monitoring server 101 and stored for example in a database. If the cud chews decrease to a critical level, the animal monitoring server 101 can send an alert to a user. The alert can be SMS, email, phone message or alarm to a phone 124 or other device 125. The alert can be sent to whoever wishes to see it or to whoever someone else wishes to receive it.

The animal monitoring server 101 protocols for the alerts can be established and the rules can be manipulated by the end user. The rules will be sent to the central database, then the instructions shall determine what packets of data are required to be collected, stored or sent. The display of this data can be in the form of graphs, tables or numbers on a user interface. In respect of alerts, it can be the animation of the cow number or name, a voice message, or an alarm.

In another embodiment the animal monitoring server 101 would store the data locally and monitor for an unwell animal and then send the alarm data only if the animal is unwell. This may be used if one of the communications channels is expensive to send data over. The stored data could be collected when for example the animals come into the yards or when a drone flies over. However the un-wellness data which is important would be sent immediately over the more expensive channel.

Deer Velvet Estimator

In a further embodiment the animal monitoring server will be able to evaluate and monitor the rate of velvet growth. Referring to FIG. 5 which shows a deer in order to estimate the rate of growth of deer velvet an additional monitor or sensor 501 (the velvet sensor ($r_2$)) similar to the animal monitor 201 would be attached to the antlers of a deer. The animal monitor 201 would be attached to the deer's ear. The additional monitor 501 (the velvet monitor) may have similar functionality the animal monitor 201 or may have more limited features, for example its communication module may only be able to communicate with the animal monitor 201.

To calculate the velvet growth the animal monitoring server 101 may send a request for data collection to the animal monitoring tag 201 (the ear tag ($r_1$)), which operates as a transceiver. In an alternative embodiment the animal monitor 201 may be programmed to periodically collect data on velvet growth.

In order to collect the data on velvet growth the animal monitor 201 (ear tag sensor ($r_1$)) sends a query to sensor 501 (the velvet sensor ($r_2$)) to initiate data exchange.

Figure 3:
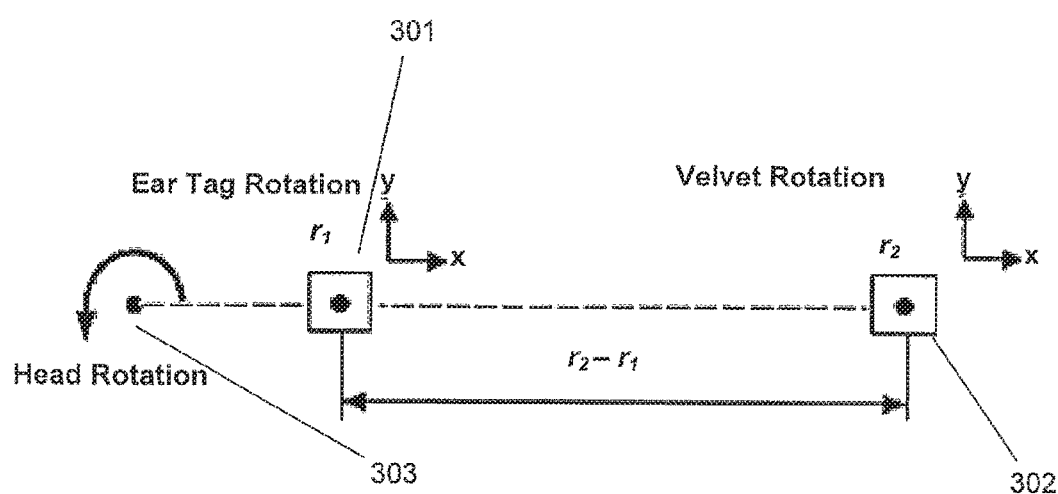
FIG. 3 is an illustration of the velvet monitoring method of the present invention.

Referring to FIG. 3 the sensors 201, 501 with accelerometers are mounted on the ear tag and rigidly attached to the velvet at distance $r_1$ 301 and $r_2$ 302 from the head rotation point 303.

It is known that the radial acceleration measured by accelerometer $r_1$ is $$a_1 = w^2 r_1$$

where w is angular velocity and the radial acceleration measured by accelerometer $r_2$ is $$a_2 = w^2 r_2$$

The difference between the two measurements $$a_2 - a_1 = w^2 (r_2 - r_1)$$

So the measurement of difference D is a2–a1 if both accelerometers' have the same angular velocity, which can be measured as the rate of the ear tag rotation. This difference being D will then be proportional to the distance or length from the ear sensor $r_1$ 301 to the rigidly placed sensor on the velvet $r_2$ 302 and ultimately is proportional to the velvet length.

Once we have D is it possible to use a lookup table to calculate the growth in cm or can we look up a previous D to identify the percentage of growth since last measured?

Wellbeing

Wellbeing is the normal or abnormal condition of intrinsic attributes of a physical state and physiological state and is accessed by measuring the physiological system responses to a primary factor of life. In particular the gravitational forces asserted on a body. Combined the variances observed provides an overall picture of the physical and physiological states of a body and these observations can then be bench-marked against known traits of wellbeing.

In the present invention the attributes of a spectrum of the oscillations or repetitive action of the system of mass, for example the locomotion of the animal body, working against or as a result of applied gravity force are used as a measure of wellbeing of the animal. The animal monitor using at least one 3 axis accelerometer can make these measurements. The points of measurement may be located at any physical location on the body, and these locations and the number of these locations are determined by a test object and the task of the test. In the preferred embodiment these measurements are made using the animal monitor 201 but in an alternative embodiment a plurality of monitors may be used.

The segments of reaction can manifest information about dynamic properties and intrinsic conditions of such animals and the compactness of the data representation provides opportunities for the study of hidden processes, a new way of interpreting the results, data exchange and storage. The lengthy data can be substituted with parameters and statistical factors or with set of data, which correspond to several measuring point in the test.

Wellbeing rank essentially is descriptors of the spectral characteristics of the specific forces acting of body during the movements and could be evaluating in several forms. In one embodiment wellbeing rank was evaluated as spectral centroid but the present invention is not limited to the spectral centroid and other forms of spectral classification could be used.

The spectral centroid is calculated as the weighted mean of the frequencies present in the signal of acceleration or in the signal of specific forces acting upon the body, determined using a Fourier transform, with their magnitudes as the weights:

$$\text{Wellbeing Rank} = \frac{\sum_{n=0}^{N-1} f(n)x(n)}{\sum_{n=0}^{N-1} x(n)}$$

Where x(n) represents the weighted frequency value, or magnitude, of bin number n, and f(n) represents the centre frequency of that bin.

The wellness rank would in one embodiment be calculated by the animal monitoring server 101 based on data supplied by the animal monitor 201.

While the present invention has been illustrated by the description of the embodiments thereof, and while the embodiments have been described in detail, it is not the intention of the Applicant to restrict or in any way limit the scope of the appended claims to such detail. Further, the above embodiments may be implemented individually, or may be combined where compatible. Additional advantages and modifications, including combinations of the above embodiments, will readily appear to those skilled in the art. Therefore, the invention in its broader aspects is not limited to the specific details, representative apparatus and methods, and illustrative examples shown and described. Accordingly, departures may be made from such details without departure from the spirit or scope of the Applicant's general inventive concept.

What we claim is:

1. An animal monitor comprising:
    a microcontroller;
    at least one three-axis accelerometer, in communication with the microcontroller, the at least one three-axis accelerometer providing data to the microcontroller;
    an energy source for powering the monitor;
    a charger for charging the energy source; and
    a communications system, associated with the microcontroller, the communications system including a wireless transmitter and receiver,
    wherein the animal monitor is configured to attach to an animal,
    wherein the microcontroller is programmed to analyse the data to calculate information on the animal with the animal monitor attached, and
    wherein the information includes the wellbeing of the animal the animal monitor is attached to, and wherein the wellbeing of an animal is calculated using a spectral centroid calculated as the weighted mean of the frequencies present in the signal of acceleration using a Fourier transform, with the magnitudes as the weights:

$$\text{Wellbeing Rank} = \frac{\sum_{n=0}^{N-1} f(n)x(n)}{\sum_{n=0}^{N-1} x(n)}$$

where x(n) represents the weighted frequency value, or magnitude, of bin number n, and f(n) represents the centre frequency of that bin, the frequencies being the number of oscillations of a norm of acceleration per unit of time.

2. The animal monitor as claimed in claim 1 wherein the monitor additionally includes a least one sound sensor in communication with the microcontroller.

3. The animal monitor as claimed in claim 1 wherein the form of the animal monitor is one of the group consisting of an ear tag, a collar, a necklace, and an implant.

4. The animal monitor as claimed in claim 1 wherein the microcontroller is programmed to monitor characteristics of an animal.

5. The animal monitor as claimed in claim 1 wherein the microcontroller is programmed to record data including at least one of the frequency of acceleration during movement and the distance travelled.

6. The animal monitor as claimed in claim 1 wherein the microcontroller is programmed to calculate information on the animal with the animal monitor attached including monitoring a cud chewing frequency of the animal.

7. The animal monitor as claimed in claim 6 wherein the microcontroller is programmed to raise an alarm if the cud chewing frequency of the animal drops below a desired level.

8. The animal monitor as claimed in claim 1 wherein the microcontroller is programmed to:
    receive data on the growth of the animal antlers; and
    calculate information on the growth of the antlers based on the received data.

9. The animal monitor as claimed in claim 1 wherein the microcontroller is programmed to receive and store data on the animal from other data sources.

10. The animal monitor as claimed in claim 9 wherein the other data sources include a scale for measuring weight.

11. A method of monitoring at least one animal using a processor, the method comprising the steps of:
    receiving data from at least one animal monitor attached to an animal;

storing the data in association with an identifier of the animal that the animal monitor is attached to; and analysing the data to calculate information on the animal with the animal monitor attached, wherein the information includes at least the weight of the animal determined based on monitoring movement of the animal including at least one of the animal walking or running and based on conversion of potential energy to kinetic energy during the movement of the animal; and wherein the information includes the wellbeing of the animal the animal monitor is attached to, wherein the wellbeing of an animal is calculated using a spectral centroid calculated as the weighted mean of the frequencies present in the signal of acceleration using a Fourier transform, with the magnitudes as the weights:

$$\text{Wellbeing Rank} = \frac{\sum_{n=0}^{N-1} f(n)x(n)}{\sum_{n=0}^{N-1} x(n)}$$

where x(n) represents the weighted frequency value, or magnitude, of bin number n, and f(n) represents the centre frequency of that bin, the frequencies being the number of oscillations of a norm of acceleration per unit of time.

12. The method of monitoring at least one animal as claimed in claim 11 including the steps of:
   receiving data on the growth of the animal antlers; and
   calculating information on the growth of the antlers based on the received data.

13. The method of monitoring at least one animal as claimed in claim 11 including the step of receiving and storing data on the animal from other data sources.

14. The method of monitoring at least one animal as claimed in claim 13 wherein the other data sources include a scale for measuring weight.

15. An animal monitoring system comprising:
   a processor;
   memory;
   storage; and
   a communication device,
the processor programmed to:
   receiving data from at least one animal monitor attached to an animal;
   storing the data in association with an identifier of the animal that the animal monitor is attached to; and
   analysing the data to calculate information on the animal with the animal monitor attached,
wherein the information calculated includes the wellbeing of the animal the animal monitor is attached to, and wherein the wellbeing of an animal is calculated using a spectral centroid calculated as the weighted mean of the frequencies present in the signal of acceleration using a Fourier transform, with the magnitudes as the weights:

$$\text{Wellbeing Rank} = \frac{\sum_{n=0}^{N-1} f(n)x(n)}{\sum_{n=0}^{N-1} x(n)}$$

where x(n) represents the weighted frequency value, or magnitude, of bin number n, and f(n) represents the centre frequency of that bin, the frequencies being the number of oscillations of a norm of acceleration per unit of time.

16. The animal monitoring system as claimed in claim 15 wherein the processor is programmed to calculate information on the animal with the animal monitor attached including monitoring a cud chewing frequency of the animal.

17. The animal monitoring system as claimed in claim 16 wherein the processor is programmed to raise an alarm if the cud chewing frequency of the animal drops below a desired level.

18. The animal monitoring system as claimed in claim 15 wherein the processor is programmed to:
   receive data on the growth of the animal antlers; and
   calculate information on the growth of the antlers based on the received data.

19. The animal monitoring system as claimed in claim 15 wherein the processor is programmed to receive and store data on the animal from other data sources.

20. The animal monitoring system as claimed in claim 19 wherein the other data sources include a scale for measuring weight.

21. The animal monitor as claimed in claim 1 wherein the microcontroller is programmed to raise an alarm if the wellbeing rank of the animal drops below a desired level.

22. The method of monitoring at least one animal as claimed in claim 11 including the step of raising an alarm if the wellbeing rank of the animal drops below a desired level.

23. The animal monitor as claimed in claim 15 wherein the processor is programmed to raise an alarm if the wellbeing rank of the animal drops below a desired level.

24. The animal monitor as claimed in claim 7 wherein the microcontroller is programmed to raise an alarm if the wellbeing rank of the animal drops below a desired level.

25. The animal monitor as claimed in claim 17 wherein the processor is programmed to raise an alarm if the wellbeing rank of the animal drops below a desired level.

26. The animal monitor as claimed in claim 10 wherein the microcontroller is programmed to raise an alarm if the wellbeing rank of the animal drops below a desired level.

27. The method of monitoring at least one animal as claimed in claim 14 including the step of raising an alarm if the wellbeing rank of the animal drops below a desired level.

28. The animal monitor as claimed in claim 20 wherein the processor is programmed to raise an alarm if the wellbeing rank of the animal drops below a desired level.

* * * * *